United States Patent
Soo et al.

(10) Patent No.: US 7,549,860 B2
(45) Date of Patent: Jun. 23, 2009

(54) HAND INSTRUMENT FOR DETACHING ORTHODONTIC BRACKETS FROM TEETH

(75) Inventors: Philip P. Soo, Fullerton, CA (US); Fay T. Salmon, Eden Prairie, MN (US); John A. Verdouw, Ontario, CA (US); Ming-Lai Lai, Arcadia, CA (US); James D. Clearly, Glendora, CA (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 11/010,889

(22) Filed: Dec. 13, 2004

(65) Prior Publication Data

US 2006/0127835 A1   Jun. 15, 2006

(51) Int. Cl.
*A61C 7/00* (2006.01)
(52) U.S. Cl. .......................................... 433/4
(58) Field of Classification Search .................. 433/4, 433/3, 9, 157
See application file for complete search history.

(56) References Cited

U.S. PATENT DOCUMENTS

| | | | |
|---|---|---|---|
| 3,507,043 A | 4/1970 | Rubin | |
| 3,755,902 A | 9/1973 | Northcutt | |
| 3,871,098 A | 3/1975 | Dean | |
| 3,986,265 A | 10/1976 | Cusato | |
| 4,035,919 A | 7/1977 | Cusato | |
| 4,155,164 A | 5/1979 | White | |
| 4,202,328 A * | 5/1980 | Sukkarie | 433/18 |
| 4,248,587 A | 2/1981 | Kurz | |
| 4,455,138 A | 6/1984 | Sheridan | |
| 4,478,576 A | 10/1984 | Maijer | |
| 4,553,932 A | 11/1985 | Armstrong et al. | |
| 4,631,028 A | 12/1986 | Kurz | |
| 4,669,979 A | 6/1987 | Snead | |
| 4,776,791 A | 10/1988 | Hannula et al. | |
| 4,850,864 A | 7/1989 | Diamond | |
| 4,875,855 A | 10/1989 | Beckett | |
| 4,904,183 A | 2/1990 | Hannan et al. | |
| 4,907,965 A | 3/1990 | Martin | |
| 4,921,423 A | 5/1990 | Kesling | |
| 4,950,157 A * | 8/1990 | Cleary | 433/4 |
| 5,035,612 A | 7/1991 | Martin et al. | |
| 5,062,793 A | 11/1991 | Cleary et al. | |
| 5,098,288 A * | 3/1992 | Kesling | 433/9 |
| 5,263,859 A * | 11/1993 | Kesling | 433/9 |
| 5,366,372 A | 11/1994 | Hansen et al. | |
| 5,380,196 A | 1/1995 | Kelly et al. | |
| 5,439,379 A | 8/1995 | Hansen | |
| 6,382,965 B1 * | 5/2002 | Ruiz-Vela et al. | 433/4 |
| 6,474,988 B1 | 11/2002 | Georgakis et al. | |
| 2005/0123875 A1 | 6/2005 | Stadtmiller et al. | |

* cited by examiner

*Primary Examiner*—Ralph A Lewis
(74) *Attorney, Agent, or Firm*—Phillip P. Soo

(57) ABSTRACT

A hand instrument for debonding an adhesively bonded orthodontic bracket from a patient's tooth includes two jaws, each of which includes a contact pad for engaging opposite sides of the bracket. When the jaws are moved together, at least a majority of the area of each contact pad that contacts the side of the bracket is located beneath the archwire slot of the bracket in a lingual direction in order to facilitate fracture of the adhesive bond and release of the bracket from the tooth surface.

5 Claims, 5 Drawing Sheets

HAND INSTRUMENT FOR DETACHING ORTHODONTIC BRACKETS FROM TEETH

BACKGROUND OF THE INVENTION

1. Field of the Invention

This invention relates to a hand tool for use with orthodontic brackets that are directly secured to the enamel surfaces of teeth by an adhesive. More particularly, the present invention relates to a hand instrument for detaching orthodontic brackets from teeth as well as methods for detaching orthodontic brackets from teeth.

2. Description of the Related Art

Orthodontic treatment is directed to movement of malpositioned teeth to improved positions in the oral cavity. Orthodontic treatment can greatly enhance the patient's facial appearance, especially in areas near the front of the patient's mouth. Orthodontic treatment can also improve the patient's occlusion so that the teeth function better with each other during mastication.

One type of orthodontic treatment involves the use of a set of appliances and archwires that are commonly known collectively as "braces". During treatment, tiny slotted appliances known as brackets are affixed to the patient's anterior, cuspid and bicuspid teeth, and an archwire is placed in the slot of each bracket. The archwire forms a track to guide movement of the teeth to orthodontically correct positions. Ends of the archwire are often received in the passages of small appliances known as buccal tubes that are affixed to the patient's molar teeth.

In the past, orthodontic brackets were commonly welded or brazed to bands that were placed around the teeth. Today, orthodontic brackets are often bonded directly to the enamel surface of the teeth by an adhesive. Once treatment has been completed, the archwire is removed from the slots of the brackets and each bracket is then removed from the associated tooth.

Orthodontic brackets are typically made of metal, ceramic or plastic. Improved ceramic brackets are described in U.S. Pat. Nos. 5,439,379 and 5,366,372. The ceramic brackets described in those patents have two sections that are spaced apart from each other by a channel. In some of the embodiments described in these patents, the bracket sections are connected to each other by a thin web of material that lies along the bottom of the channel and is next to a layer of adhesive that bonds the bracket to the tooth.

The brackets that are described in U.S. Pat. Nos. 5,439,379 and 5,366,372 are debonded from the surface of the teeth at the conclusion of treatment by urging the sections in directions toward each other. Hand instruments that are especially useful for debonding such brackets are described in those patents as well as in U.S. Pat. No. 6,474,988. These hand instruments include wall portions for engaging the sides of the bracket so that the sections of the bracket pivot toward each other and away from the tooth surface when handles of the hand instrument are squeezed together.

There is a continuing need in the art to ensure that all brackets, whether made of ceramic, plastic or metallic materials, are easily debonded from the teeth in a consistent manner at the conclusion of treatment. If, for example, the brackets are constructed to debond from the teeth when sections of the bracket are pivoted together, it is preferable that the sections consistently release from the enamel surface of the teeth in a predictable manner and without undue force. Oftentimes, the patient's teeth are sensitive at the conclusion of orthodontic treatment and for this reason it is desirable to avoid undue pressure or force on the teeth if at all possible.

SUMMARY OF THE INVENTION

The present invention is directed toward improved methods and apparatus for debonding orthodontic brackets from teeth. The apparatus comprises a hand instrument that includes two contact pads for engaging certain regions of the sides of the bracket during a debonding procedure. The contact pads facilitate fracture of the adhesive bond between the bracket and the tooth enamel, while tending to reduce the amount of stress that might otherwise be exerted on the bracket.

Preferably, the two contact pads are provided in combination with stop portions that limit the depth of engagement of the contact pads with the sides of the bracket. The stop portions help to position the contact pads in preferred locations, such as locations wherein at least 50% of the area of the contact pads is beneath the archwire slot of the bracket in a lingual direction.

In more detail, the present invention in one aspect is directed to a hand instrument for debonding an orthodontic bracket. The hand instrument comprises a first jaw including a contact pad for engaging a mesial side of the bracket, and a second jaw that is movable relative to the first jaw. The second jaw includes a contact pad for engaging a distal side of the bracket. At least one of the jaws includes a stop for limiting the depth of engagement in a lingual direction of the contact pads with the respective sides of the bracket. The contact pads are spaced from the facial edge of the mesial side and the distal side of the bracket when the contact pads have reached the limit of their depth of engagement in a lingual direction with the respective sides of the bracket.

Another aspect of the invention is also directed to a hand instrument for debonding an orthodontic bracket. This hand instrument comprises a first jaw including a contact pad for engagement with a mesial side of a bracket, and a second jaw that is movable relative to the first jaw. The second jaw includes a contact pad for engaging a distal side of the bracket. At least one of the jaws includes a stop for limiting the depth of engagement in a lingual direction of the contact pads with the respective sides of the bracket. At least 50% of the area of the contact pads is located beneath the archwire slot of the bracket in a lingual direction when the contact pads have reached the limit of their depth of engagement in a lingual direction with the respective sides of the bracket.

The present invention is also directed in yet another aspect toward a hand instrument for debonding an orthodontic bracket. This hand instrument comprises a first jaw including a contact pad for engaging a mesial side of a bracket, and a second jaw that is movable relative to the first jaw. The second jaw includes a contact pad for engaging a distal side of the bracket. At least one of the jaws includes a stop for limiting the depth of engagement in a lingual direction of the contact pads with the respective sides of the bracket. The contact pads extend inwardly in respective directions toward each other such that a space is presented between the hand instrument and the bracket in regions location facially of the contact pads when the contact pads have reached the limit of their depth of engagement in a lingual direction with the respective sides of the bracket.

The present invention is also directed toward a method of detaching an orthodontic bracket having mesial and distal sections from a tooth. The method comprises:

engaging a mesial side of the mesial section with a first contact pad of a hand instrument at a location spaced from the facial edge of the mesial side;

engaging a distal side of the distal section with a second contact pad of the hand instrument at a location spaced from the facial edge of the distal side; and urging the first contact pad and the second contact pad in directions toward each other in order to pivot at least one of the mesial and distal sections away from the tooth.

Another aspect of the present invention is also directed toward a method of detaching an orthodontic bracket having mesial and distal sections from a tooth. This method comprises:

engaging a mesial side of the mesial section with a first contact pad of a hand instrument, wherein at least 50% of the area of the first contact pad is located beneath the archwire slot of the bracket in a lingual direction;

engaging a distal side of the distal section with a second contact pad of the hand instrument, wherein at least 50% of the area of the second contact pad is located beneath the archwire slot of the bracket in a lingual direction; and urging the first contact pad and the second contact pad in directions toward each other in order to pivot at least one of the mesial and distal sections away from the tooth.

Still another aspect of the invention is also directed toward a method of detaching an orthodontic bracket from a tooth. This method comprises:

engaging a mesial side of a mesial tiewing of the bracket with a first jaw in a location spaced from an archwire slot of the bracket;

engaging a distal side of a distal tiewing of the bracket with a second jaw in a location spaced from an archwire slot of the bracket; and urging the jaws in a direction toward each other in order to deform the bracket and fracture the adhesive bond between the bracket and the tooth.

Additional details and aspects of the invention are set out in the description that follows and are illustrated in the accompanying drawings.

DEFINITIONS

Figure 1:
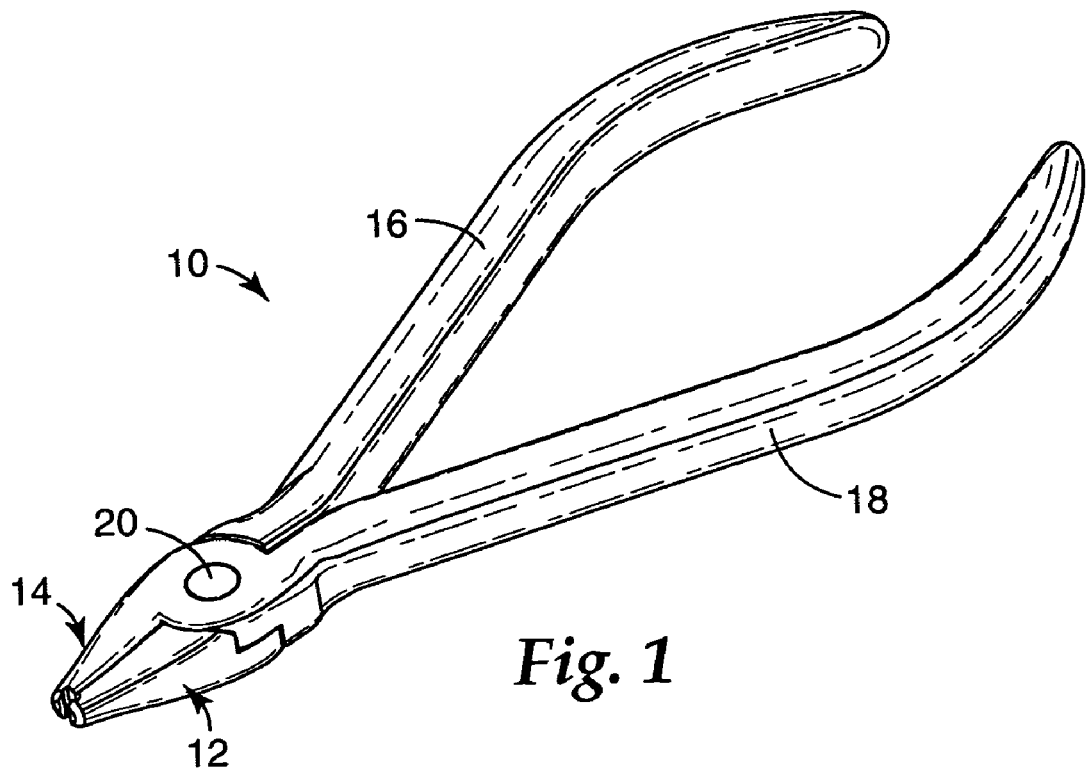
FIG. 1 is a perspective view of a hand instrument for detaching orthodontic brackets from teeth according to one embodiment of the invention.
Figure 2:
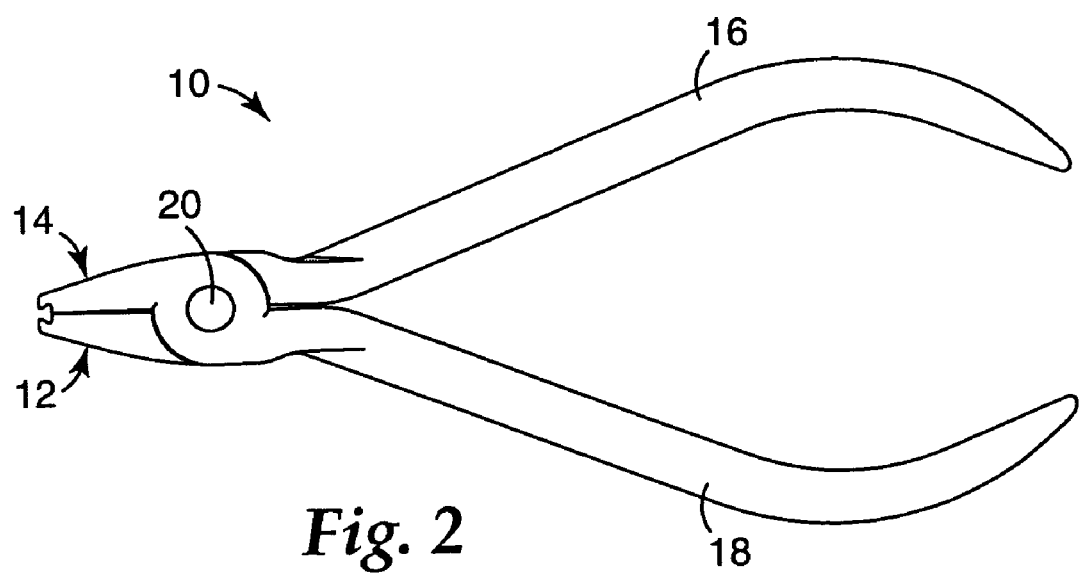
FIG. 2 is a side elevational view of the hand instrument shown in FIG. 1.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" and "buccolabial" mean in a direction toward the patient's cheeks or lips.

"Lingual" means in a direction toward the patient's tongue.

DETAILED DESCRIPTION OF THE PREFERRED EMBODIMENTS

A hand instrument for debonding orthodontic brackets that is constructed according to one embodiment of the invention is illustrated in FIGS. 1-6 and is broadly designated by the numeral 10. The hand instrument 10 includes a first jaw 12 and a second jaw 14. The hand instrument 10 also includes a first handle 16 that is integrally connected to the first jaw 12 and a second handle 18 that is integrally connected to the second jaw 14.

The first jaw 12 is movably connected to the second jaw 14 by a pivot 20. As the handles 16, 18 are squeezed together, the outer tips of the jaws 12, 14 (i.e., the tips of the jaws remote from the handles 16, 18) move toward each other along respective curved paths.

Figure 3:
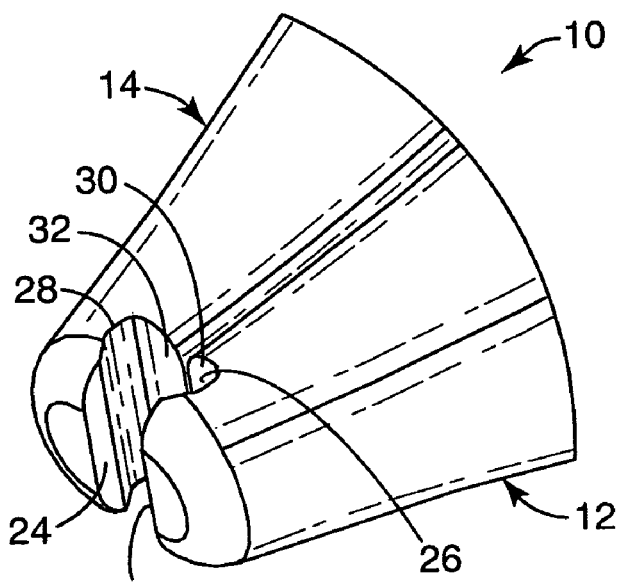
FIG. 3 is an enlarged perspective view of a front portion of the hand instrument shown in FIGS. 1 and 2, illustrating portions of two jaws of the hand instrument.
Figure 4:
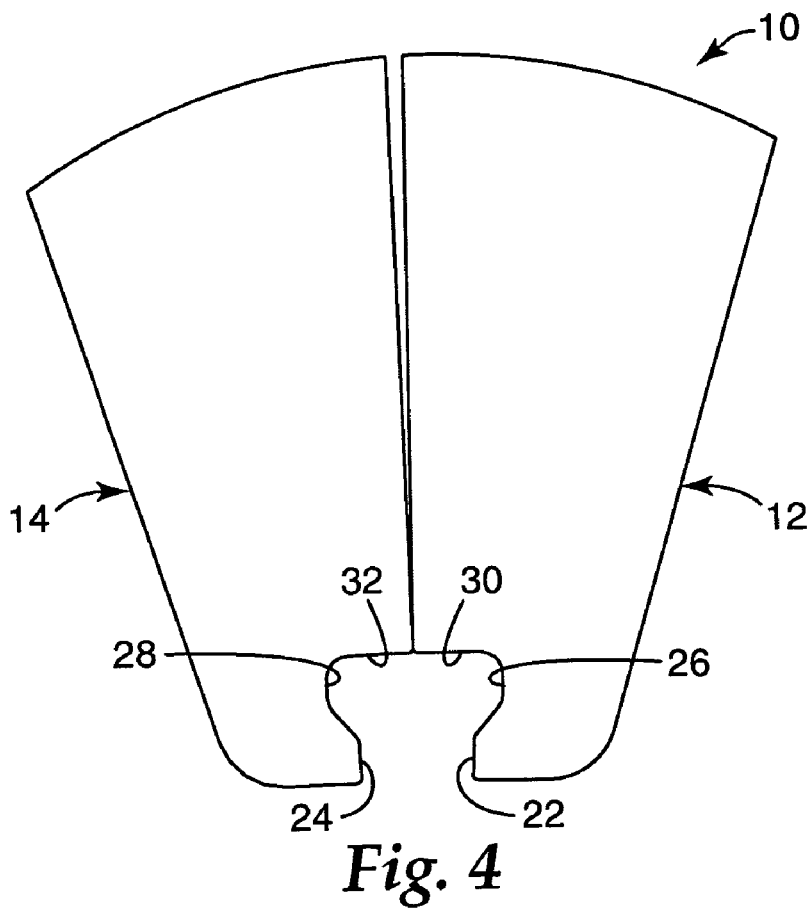
FIG. 4 is an enlarged side elevational view of the jaw portions that are depicted in FIG. 3.

The front tip portions of the jaws 12, 14 are shown in enlarged view in FIGS. 3 and 4. As illustrated, the first jaw 12 includes a first contact pad 22 and the second jaw 14 includes a second contact pad 24. Both of the contact pads 22, 24 include flat walls that face each other and are located at the outermost ends of the first jaw 12 and second jaw 14, respectively. Contact pads 22, 24 are elongated and extend in directions parallel to each other and parallel to the pivot axis of the pivot 20.

The first jaw 12 also includes a first groove 26 that extends alongside the first contact pad 22. The second jaw 14 includes a second groove 28 that extends alongside the second contact pad 24. As shown for example in FIG. 4, the contact pads 22, 24 are spaced apart from each other a certain distance when the jaws 12, 14 are fully closed. Moreover, the bottoms of the grooves 26, 28 are spaced apart a distance that is greater than the distance between the contact pads 22, 24 when the jaws 12, 14 are closed. As illustrated for example in FIG. 3, the grooves 26, 28 have a longitudinal axis that extends in a direction parallel to the longitudinal axis of the respective, adjacent contact pad 22, 24.

The first jaw 12 also includes a first stop portion 30 that extends next to the first groove 26. The second jaw 14 includes a second stop portion 32 that extends next to the second groove 28. When the jaws 12, 14 are closed, the stop portions 30, 32 preferably extend in a common reference plane that is perpendicular or at least generally perpendicular to the facing surfaces of the contact pads 22, 24 (see, e.g., FIG. 4). The stop portions 30, 32 limit the depth of engagement of the jaws 12, 14 in a lingual direction with an orthodontic bracket during a debonding procedure as will be described in more detail in the paragraphs that follow.

Figure 5:
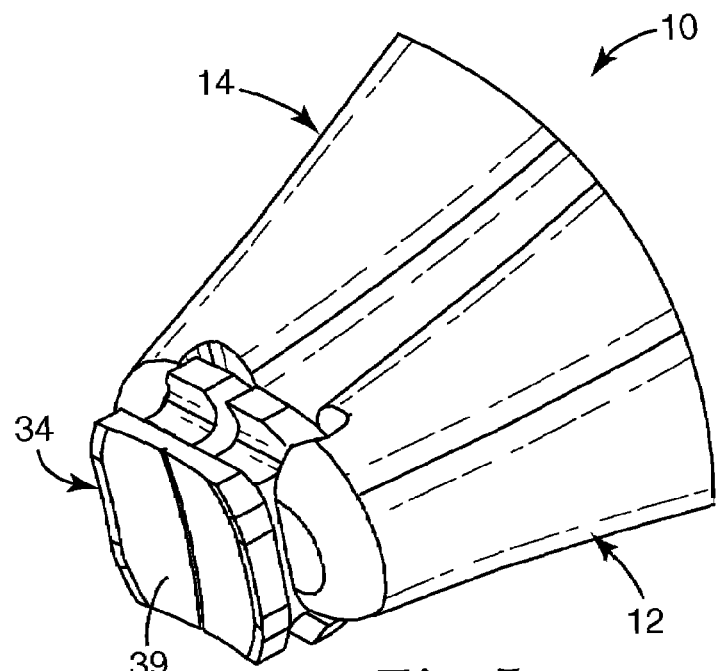
FIG. 5 is a view somewhat similar to FIG. 3 except that the jaws have been opened somewhat in order to receive an exemplary orthodontic bracket.
Figure 6:
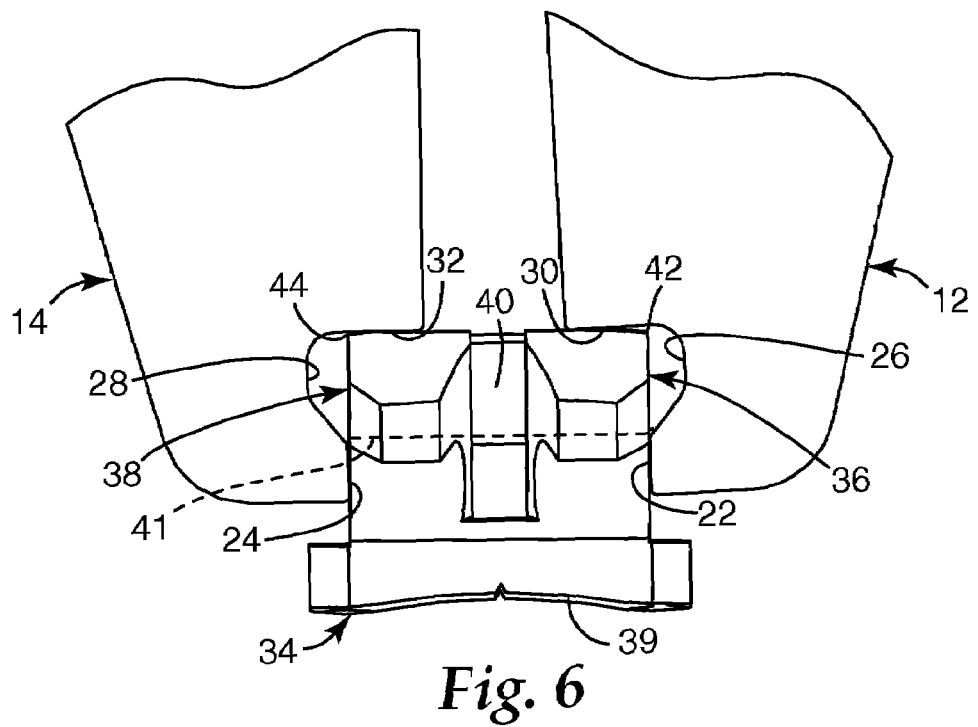
FIG. 6 is an enlarged top view of a portion of the bracket and the jaws illustrated in FIG. 5.

FIGS. 5 and 6 are illustrations showing the front tips of the jaws 12, 14 in contact with an exemplary orthodontic bracket 34. In this example, the bracket 34 is a ceramic orthodontic bracket having a mesial ceramic section 36 and a distal ceramic section 38. Each of the sections 36, 38 includes a base portion, and the two base portions together present a base 39 with a lingual surface for bonding the bracket 34 directly to the patient's tooth enamel by an adhesive.

The bracket 34 is debonded from the tooth by urging the sections 36, 38 toward each other. Examples of suitable brackets 34 include the brackets described in U.S. Pat. Nos. 5,380,196, 5,439,379, and 7,192,274. In some embodiments of the brackets described in U.S. Pat. No. 5,439,379, mesial and distal sections of the bracket are connected by a thin web of material that fractures as one or both sections pivot away from the tooth and toward the opposing section(s). However, the hand instrument 12 also may be used with other orthodontic brackets that are debonded by squeezing sections of the bracket toward each other, including other types of ceramic brackets as well as brackets made of polymeric materials or metallic materials.

FIG. 6 is an enlarged side elevational view of the tips of the jaws 12, 14 along with the bracket shown in FIG. 5. The view in FIG. 6 is taken in a direction looking toward a gingival side of the bracket 34. As illustrated, the bracket 34 includes an archwire slot liner 40 having an occlusal section, a lingual section and a gingival section that together define three sides of an elongated archwire slot. The archwire slot extends across a facial surface of the bracket 34 opposite the lingual surface of the bracket 34 and extends from the mesial side of the bracket 34 to the distal side of the bracket 34. The sections together present an overall, generally "U"-shaped configuration when viewed in directions along the longitudinal axis of the archwire slot.

In FIGS. 5 and 6, the jaws 12, 14 are shown as they appear when the stop portions 30, 32 are in contact with the facial surfaces of the sections 36, 38 respectively of the bracket 34. As illustrated in FIG. 6, the stop portions 30, 32 limit the depth of engagement in a lingual direction of the contact pads 22, 24 with the mesial side of the mesial section 36 and the distal side of the distal section 38 respectively. In this position of the jaws 12, 14, the contact pads 22, 24 are spaced from a facial edge 42 of the mesial side of the mesial section 36 and a facial edge 44 of the distal side of the distal section 38. Preferably, the facing external surfaces of the contact pads 22, 24 are parallel to each other when the contact pads 22, 24 engage the mesial and distal sides of a bracket having a mesial-distal width that is an average width for all of the brackets to be debonded.

The contact pads 22, 24 extend inwardly in directions toward each other such that a space is presented between the first groove 26 and the mesial side of the mesial section 36, and another space is presented between the second groove 28 and the distal side of the distal section 38. The spaces are an advantage, in that the jaws 12, 14 do not contact the sides of the bracket 34 in areas adjacent to those spaces as the jaws 12, 14 are closed. Instead, the contact pads 22, 24 bear against regions of the bracket 34 that lie at least in substantial part in a direction beneath the archwire slot (i.e., in a lingual direction) relative to the lingual side of the archwire slot. Such construction helps reduce the stress in the bracket 34 at and near the corners of the bottom of the archwire slot and in regions adjacent to the mesial and distal flanges of the bracket base 39, while also helping to introduce stress in the adhesive to facilitate adhesive fracture either along the bonding interface (adhesion fracture) or in the adhesive layer (cohesive fracture).

Preferably, at least 50% of the area of the contact pads 22, 24 is located beneath the archwire slot of the bracket 34 when the contact pads 22, 24 have reached the limit of their depth of engagement in a lingual direction with the sides of the mesial and distal sections 36, 38 respectively. More preferably, at least 75% of the area of the contact pads 22, 24 is located beneath the archwire slot of the bracket 34 when the contact pads 22, 24 have reached the limit of their depth of engagement in a lingual direction with the sides of the mesial and distal sections 36, 38 respectively.

Preferably, the length of the contact pads 22, 24 in an occlusal-gingival direction is substantially equal to the overall length of the side portions of the mesial and distal sections 36, 38 beneath the tiewings. In particular, the length of the contact pads 22, 24 in directions along an occlusal-gingival reference axis is substantially equal to the distance between the bottom of the ligature-receiving channel extending along the occlusal side of the bracket 34 and the bottom of the ligature-receiving channel extending along the gingival side of the bracket 34. Such construction helps ensure that the forces presented by the contact pads 22, 24 bear against the sections 36, 38 over a relatively wide area without the need to engage areas of the bracket sides adjacent to the facial edges 42, 44.

Figure 7:
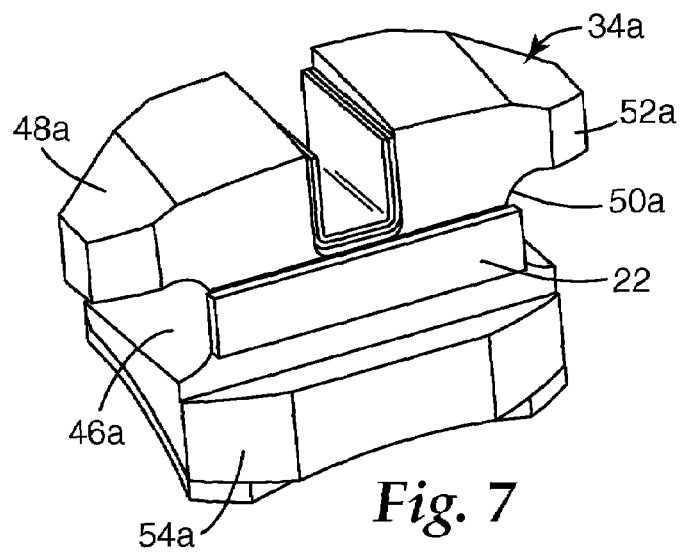
FIGS. 7-9 are reduced perspective views of portions of three exemplary orthodontic brackets along with an exemplary contact pad of a hand instrument of the present invention, illustrating the location of engagement of the contact pad with one side of each bracket.
Figure 8:
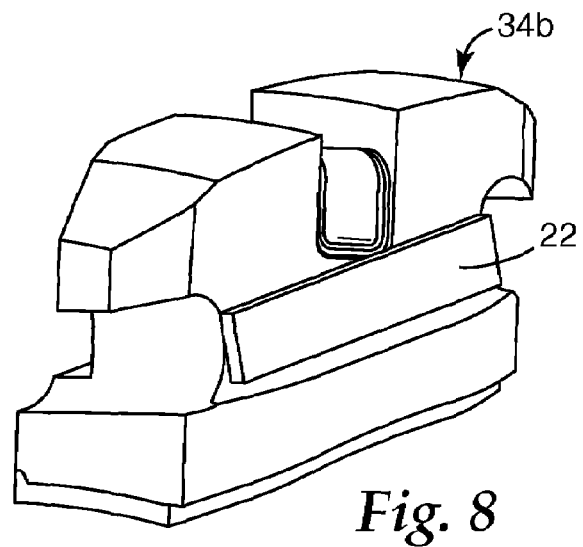
Figure 9:
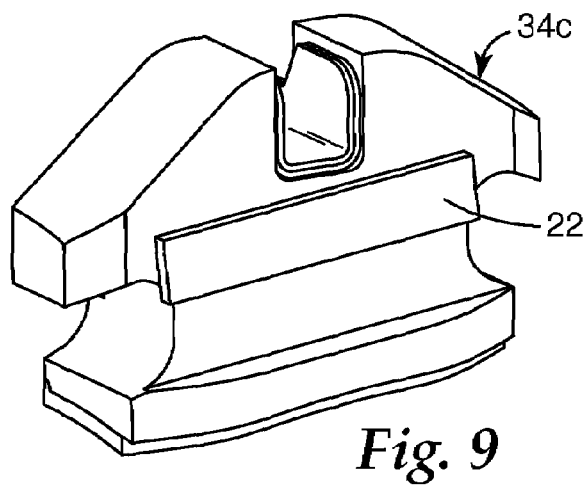

FIGS. 7-9 are exemplary illustrations of mesial sections of three different orthodontic brackets, along with only one contact pad 22 of the hand instrument 10 of the present invention for purposes of illustration. In FIG. 7, bracket 34a is a bracket intended for the patient's upper or lower cuspid tooth, and it can be observed that the entire area of the contact pad 22 lies beneath the archwire slot of the bracket 34a in a lingual direction when the contact pads have reached the limit of their depth of engagement in a lingual direction. Additionally, the contact pad 22 extends from the bottom or gingival side of a ligature channel 46a that is located in a lingual direction relative to an occlusal tiewing 48a to the bottom or occlusal side of a ligature channel 50a that is located in a lingual direction relative to a gingival tiewing 52a. Moreover, the contact pad 22 is spaced from a base flange 54a of the bracket 34a in a facial direction as well as a fillet that is next to the flange 54a in order to achieve uniform, close contact between the contact pad 22 and the side of the bracket 34a.

FIG. 8 is a view somewhat similar to FIG. 7, except that bracket 34b is an exemplary bracket intended for an upper central tooth of a patient. When used with bracket 34b, the contact pad 22 again lies in a lingual direction relative to the bottom or lingual side of the archwire slot of the bracket 34b when the contact pad 22 has reached the limit of its depth of engagement in a lingual direction with a mesial side of the bracket 34b, although the contact pad 22 is somewhat closer to the archwire slot.

FIG. 9 is a view somewhat similar to FIGS. 7 and 8, except that the bracket 34c illustrated in FIG. 9 is a bracket intended for the patient's lower anterior tooth. When used with bracket 34c, the contact pad 22 engages the mesial side of the bracket 34c in a region that is spaced from both the archwire slot as well as the archwire slot liner of the bracket 34c.

While it is possible to construct a variety of hand instruments with contact pads in different locations in accordance with shape and size of the bracket to be debonded, it has been found that a single hand instrument such as the hand instrument 10 can be used with a variety of brackets as illustrated in FIGS. 7-9 and yet achieve satisfactory results while using relatively similar forces exerted on the handles. The provision and location of the contact pads 22, 24 of the present invention helps ensure that the brackets are reliably debonded when desired, even though the size and shape of the bracket may vary.

Optionally, the contact pads 22, 24 may comprise a coating material and/or a resilient material such as the materials set out in U.S. Pat. No. 6,474,988. Optionally, the contact pads may each comprise a polymeric material that is releasably connected to the jaw by a pressure sensitive adhesive for replacement when desired. Alternatively, removable, disposable plastic sleeves may be placed over the contact pads to provide a soft surface for engaging the bracket. As another option, the contact pads 22, 24 may be provided with a certain surface roughness, cross-hatching, serrations or other surface treatment to enhance the grip of the contact pads 22, 24 on the bracket. However, in instances where the bracket is made of a ceramic material, it is presently preferred that the contact pads are made of stainless steel and are not provided with a plastic surface, surface roughness, cross-hatching or other resilient and/or friction-enhancing surface treatments.

Other options are also possible. For example, the jaws 12, 14 could be provided with a shield having a configuration sufficient to surround the bracket during a debonding procedure. The shield is adapted to contain fragments or sections of the bracket that might otherwise become loose in the oral cavity during a debonding procedure. Exemplary shields are described, for example, in U.S. Pat. No. 6,474,988.

Figure 10:
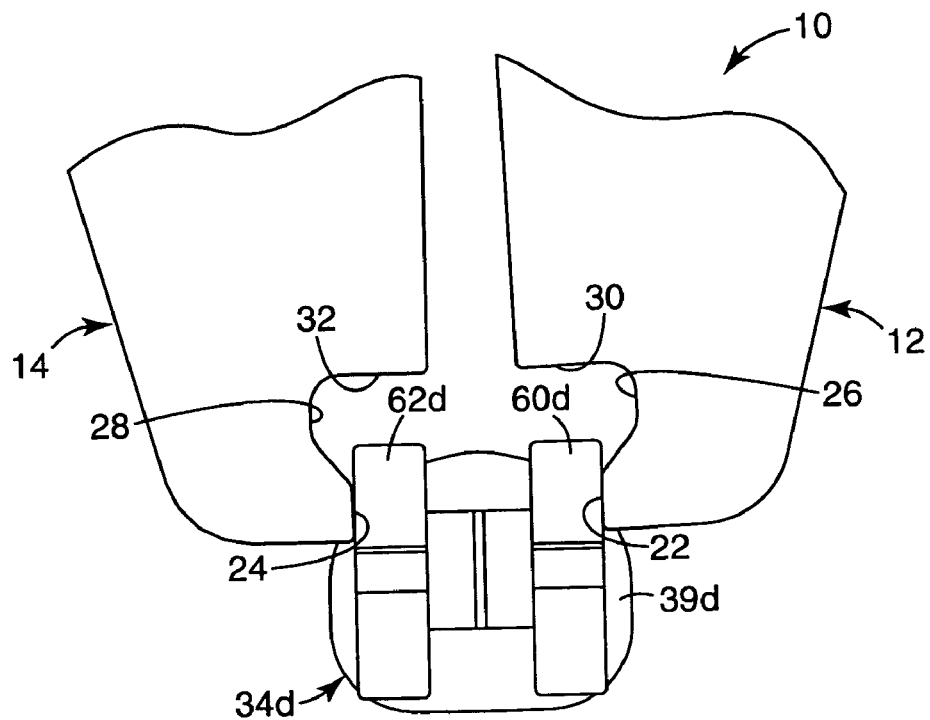
FIG. 10 is an enlarged side elevational view of a portion of the jaws of the hand instrument along with a different exemplary bracket, wherein the jaws are oriented in a different position relative to the bracket as compared to the orientation of the jaws shown in FIG. 5.

The hand instrument 10 may also be used in an orientation different than the orientation shown in FIGS. 5 and 6. For example, the hand instrument 10 may be used as shown in FIGS. 5 and 6 except that the contact pads 22, 24 are moved in either an occlusal or a gingival direction, such that the contact pads 22, 24 are located in an occlusal or gingival direction relative to the archwire slot and at least 50% of the area of the contact pads is located below the archwire slot in a lingual direction. As another example, and as shown in FIG. 10, the hand instrument 10 may be oriented such that the longitudinal axis of the contact pads 22, 24 extends in a generally buccolabial-lingual direction, and the contact pads are located to one side of the archwire slot of the bracket 34d. In the example shown in FIG. 10, the contact pads 22, 24 engage the mesial side of the mesial-occlusal tiewing 60d of the bracket 34d and the distal side of the distal-occlusal tiewing 62d of the bracket 34d.

Figure 11:
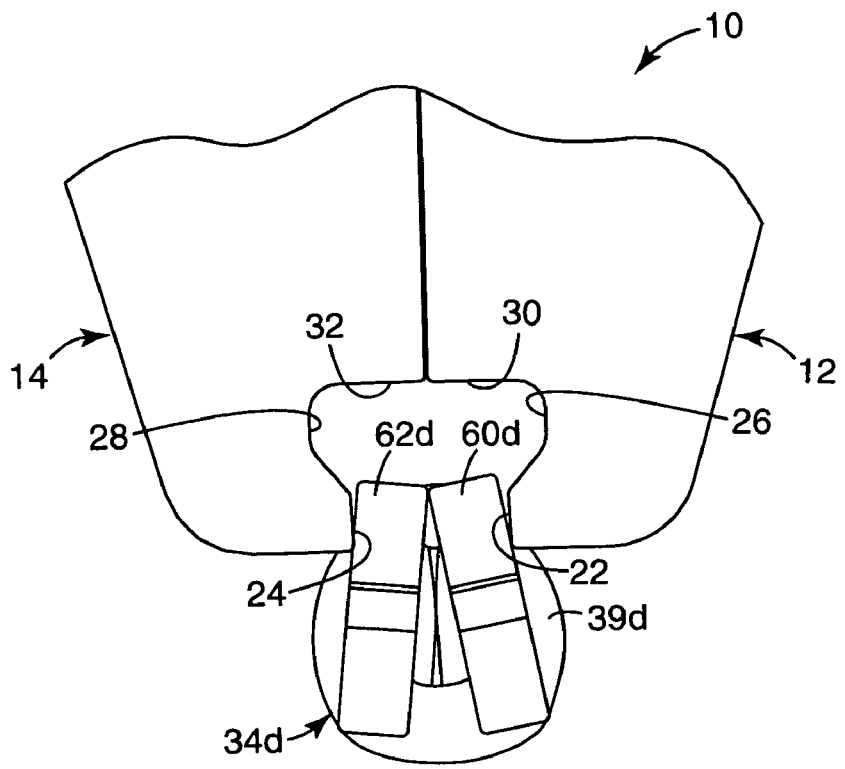
FIG. 11 is a view somewhat similar to FIG. 10 except that the jaws have been moved toward a closed position to deform the bracket as might occur during a debonding procedure.

As the jaws 12, 14 of the hand instrument 10 are closed as shown in FIG. 11, the mesial-occlusal tiewing 60d and distal-occlusal tiewing 62d are urged toward each other. In this example, the bracket 34d is made of a metallic material (such as stainless steel) and the bracket 34d deforms are the jaws 12, 14 are closed. As the bracket 34d deforms, the base 39d bends away from the surface of the patient's tooth and fractures the adhesive bond between the base 39d and the tooth.

Preferably, the first handle 16 and the first jaw 12 (including the first contact pad 22 and the first stop portion 30) are integrally made as a unitary component, and the second handle 18 and the second jaw 14 (including the second contact pad 24 and the second stop portion 32) are integrally made as a unitary component. Preferred materials for making such components include Series 300 and Series 400 stainless steel, including 425M stainless steel.

Optionally, the contact pads 22, 24 could each include a groove similar to the grooves provided in the jaws of the hand instrument shown in U.S. Pat. No. 5,366,372. The grooves enable the contact pads 22, 24 to be placed on the mesial and distal sides of the bracket without removing the archwire from the archwire slot. In this manner, the time needed for removing the archwire and detaching the brackets at the conclusion of treatment can be reduced.

All of the patents and patent applications identified above are hereby expressly incorporated by reference herein. Those skilled in the art will recognize that other options, alternatives and additions are possible to the hand instrument described above without departing from the essence of our invention. Accordingly, the invention should not be deemed limited to the specific embodiments described in detail above, but instead only by a fair scope of the claims that follow along with their equivalents.

The invention claimed is:

1. A method of detaching from a tooth an orthodontic bracket having a lingual surface for bonding to the tooth, an archwire slot extending across a facial surface opposite the lingual surface extending from a mesial side of the bracket to a distal side of the bracket and opposed mesial and distal ceramic sections comprising:

engaging the mesial side of the mesial ceramic section of the bracket with a first contact pad of a hand instrument along a first contact area spaced from a facial edge of the mesial side;

engaging the distal side of the distal ceramic section of the bracket with a second contact pad of the hand instrument along a second contact area spaced from a facial edge of the distal side; and urging the first contact pad and the second contact pad in directions toward each other in order to pivot at least one of the mesial and distal ceramic sections away from the tooth and toward the opposing ceramic section(s), wherein the act of urging the first contact pad and the second contact pad in directions toward each other is carried out while avoiding contact of the hand instrument with regions of the mesial and distal sides of the bracket located between the first and second contact areas and the respective facial edges, wherein the act of engaging a mesial side of the mesial ceramic section with a first contact pad is carried out by engaging at least 50% of the area of the first contact pad with the mesial side at a location beneath the archwire slot of the bracket in a lingual direction.

2. The method of claim 1, wherein the bracket further includes a thin web of material that fractures as one or both ceramic sections pivot away from the tooth and toward the opposing section(s).

3. A method of detaching from a tooth an orthodontic bracket having a lingual surface for bonding to the tooth, an archwire slot extending across a facial surface opposite the lingual surface extending from a mesial side of the bracket to a distal side of the bracket and opposed mesial and distal ceramic sections comprising:

engaging the mesial side of the mesial ceramic section of the bracket with a first contact pad of a hand instrument along a first contact area spaced from a facial edge of the mesial side;

engaging the distal side of the distal ceramic section of the bracket with a second contact pad of the hand instrument along a second contact area spaced from a facial edge of the distal side; and urging the first contact pad and the second contact pad in directions toward each other in order to pivot at least one of the mesial and distal ceramic sections away from the tooth and toward the opposing ceramic section(s), wherein the act of urging the first contact pad and the second contact pad in directions toward each other is carried out while avoiding contact of the hand instrument with regions of the mesial and distal sides of the bracket located between the first and second contact areas and the respective facial edges, wherein the act of engaging a distal side of the distal ceramic section with a second contact pad is carried out by engaging at least 50% of the area of the second contact pad with the distal side at a location beneath the archwire slot of the bracket in a lingual direction.

4. The method of claim 3, wherein the bracket further includes a thin web of material that fractures as one or both ceramic sections pivot away from the tooth and toward the opposing section(s).

5. A method of detaching from a tooth an orthodontic bracket having a lingual surface for bonding to the tooth, an archwire slot extending across a facial surface opposite the lingual surface extending from a mesial side of the bracket to a distal side of the bracket and opposed mesial and distal sections comprising:

engaging the mesial side of the mesial section of the bracket with a first contact pad of a hand instrument along a first contact area spaced from a facial edge of the mesial side;

engaging the distal side of the distal section of the bracket with a second contact pad of the hand instrument along a second contact area spaced from a facial edge of the distal side;

urging the first contact pad and the second contact pad in directions toward each other in order to pivot at least one of the mesial and distal sections away from the tooth and toward the opposing section(s), wherein the act of urging the first contact pad and the second contact pad in directions toward each other is carried out while avoiding contact of the hand instrument with regions of the mesial and distal sides of the bracket located between the first and second contact areas and the respective facial edges; and contacting a stop portion of the hand instrument against the facial surface of the bracket during the act of urging the first contact pad and the second contact pad in directions toward each other, wherein the act of engaging a mesial side of the mesial section with a first contact pad is carried out by engaging at least 50% of the area of the first contact pad with the mesial side at a location beneath the archwire slot of the bracket in a lingual direction, and wherein the act of engaging a distal side of the distal section with a second contact pad is carried out by engaging at least 50% of the area of the second contact pad with the distal side at a location beneath the archwire slot of the bracket in a lingual direction.

\* \* \* \* \*

UNITED STATES PATENT AND TRADEMARK OFFICE
CERTIFICATE OF CORRECTION

PATENT NO. : 7,549,860 B2  Page 1 of 1
APPLICATION NO. : 11/010889
DATED : June 23, 2009
INVENTOR(S) : Philip P. Soo It is certified that error appears in the above-identified patent and that said Letters Patent is hereby corrected as shown below:

On the Title Page
Item (75) (Inventors), Delete "James D. Clearly" and insert -- James D. Cleary --, therefor.
Item (74) (Attorney), Delete "Phillip P. Soo" and insert -- Philip P. Soo --, therefor.

Signed and Sealed this

Eighteenth Day of August, 2009

David J. Kappos
*Director of the United States Patent and Trademark Office*